(12) United States Patent
Aryan et al.

(10) Patent No.: US 9,145,421 B2
(45) Date of Patent: Sep. 29, 2015

(54) PROCESS FOR THE PREPARATION OF ASENAPINE MALEATE

(75) Inventors: Ram Chander Aryan, New Delhi (IN); Anamika Mishra, Puruliya (IN); Pudi Giri Jagannadha Naidu, Vizakhapatnam (IN); Ramnik Sharma, Gurgaon (IN)

(73) Assignee: RANBAXY LABORATORIES LIMITED, New Delhi (IN)

( * ) Notice: Subject to any disclaimer, the term of this patent is extended or adjusted under 35 U.S.C. 154(b) by 10 days.

(21) Appl. No.: 14/233,284

(22) PCT Filed: Jul. 17, 2012

(86) PCT No.: PCT/IB2012/053652
§ 371 (c)(1),
(2), (4) Date: Aug. 20, 2014

(87) PCT Pub. No.: WO2013/011461
PCT Pub. Date: Jan. 24, 2013

(65) Prior Publication Data
US 2015/0112083 A1    Apr. 23, 2015

(30) Foreign Application Priority Data
Jul. 20, 2011 (IN) .......................... 2042/DEL/2011

(51) Int. Cl.
C07D 491/044    (2006.01)

(52) U.S. Cl.
CPC ................................. C07D 491/044 (2013.01)

(58) Field of Classification Search
None
See application file for complete search history.

(56) References Cited

U.S. PATENT DOCUMENTS

| | | | |
|---|---|---|---|
| 4,145,434 A | 3/1979 | van der Burg | 424/274 |
| 7,872,147 B2 * | 1/2011 | Kemperman et al. | 548/421 |
| 7,956,202 B2 | 6/2011 | Kemperman et al. | 549/354 |

* cited by examiner

Primary Examiner — Michael Barker

(57) ABSTRACT

The present invention provides a process for the preparation of asenapine maleate of Formula (I), comprising: intra-molecular cyclization of the intermediate of Formula (II) to obtain the intermediate of Formula (III) using aluminium halide.

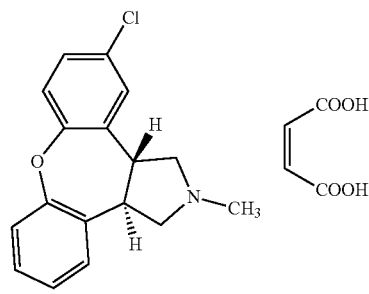

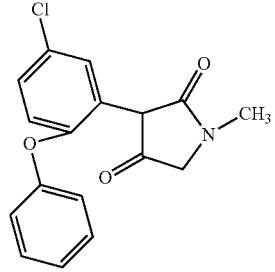

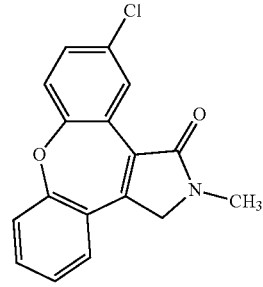

10 Claims, No Drawings

PROCESS FOR THE PREPARATION OF ASENAPINE MALEATE

FIELD OF THE INVENTION

The present invention provides a process for the preparation of asenapine maleate using aluminium halide for intramolecular cyclization.

BACKGROUND OF THE INVENTION

Asenapine and its pharmaceutically acceptable salts, including asenapine maleate, are known from U.S. Pat. No. 4,145,434. Asenapine maleate is chemically (3aRS,12bRS)-5-chloro-2-methyl-2,3,3a,12b-tetrahydro-1H-dibenzo [2,3:6,7]oxepino[4,5-c]pyrrole (2Z)-2-butenedioate (1:1), having the structure as represented by Formula I.

Formula I

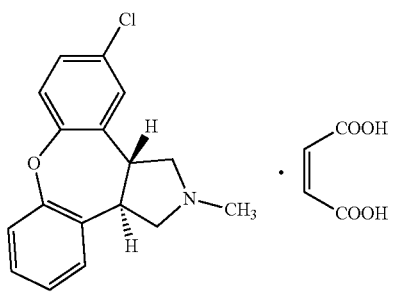

Asenapine maleate is marketed in the United States under the brand name SAPHRIS®, for the treatment of schizophrenia.

U.S. Pat. No. 4,145,434 describes a process for the preparation of asenapine by the cyclization of 3-(5-chloro-2-phenoxyphenyl)-1-methylpyrrolidine-2,4-dione (Formula II) to 11-chloro-2-methyl-2,3-dihydro-1H-dibenzo [2,3:6,7] oxepino [4,5-c]pyrrol-1-one (Formula III) using polyphosphoric acid at a temperature of 125° C.

Formula II

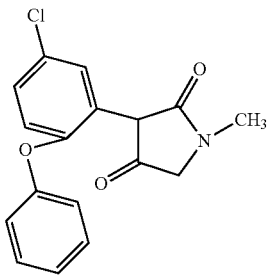

3-(5-chloro-2-phenoxyphenyl)-1-methylpyrrolidine-2,4-dione

Formula III

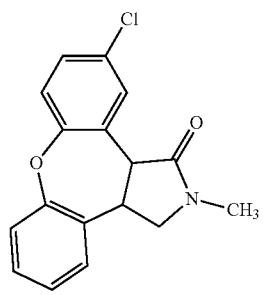

11-chloro-2-methyl-2,3-dihydro-1H-dibenzo[2,3:6,7]oxepino[4,5-c]pyrrol-1-one

U.S. Pat. No. 7,956,202 describes a process for the preparation of asenapine by the cyclization of the intermediate of Formula II to the intermediate of Formula III using hypophosphoric acid and a catalyst.

The drawbacks associated with the preparation of asenapine by the cyclization of the intermediate of Formula II to the intermediate of Formula III using prior art processes include difficulty in complete removal of phosphoric acid from the reaction mixture. This requires the use of a large amount of water for work-up and also adversely affects the yield at the next step.

Thus, there exists a need in the art for an improved and more efficient process for the cyclization of the intermediate of Formula II to the intermediate of Formula III.

SUMMARY OF THE INVENTION

The present invention provides an improved, simple, and industrially advantageous process for the cyclization of the intermediate of Formula II to the intermediate of Formula III that involves the use of aluminium halide instead of phosphoric acid. The advantages associated with the cyclization process of the present invention are:

Cyclization is carried out at a lower temperature;
Cost-effective, as it uses lower reaction volumes;
Easy work-up because phosphoric acid is not used;
No catalyst is required for carrying out cyclization; and
Better yield.

Additionally, use of borane dimethyl sulphide for the reduction of the keto group in the process of the present invention is advantageous over the use of diborane in view of its longer shelf-life.

A first aspect of the present invention provides a process for the preparation of asenapine maleate of Formula I Formula I

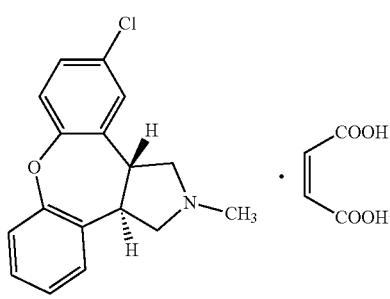

comprising:
cyclization of the intermediate of Formula II

Formula II

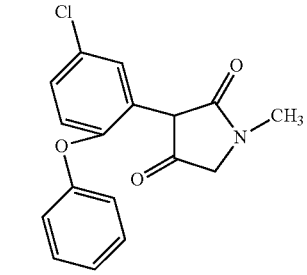

to obtain the intermediate of Formula III

Formula III

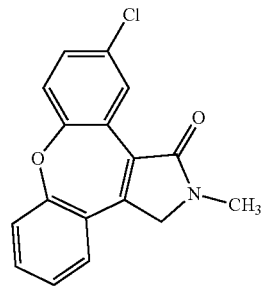

using aluminium halide.

A second aspect of the present invention provides a process for the preparation of asenapine maleate of Formula I Formula I

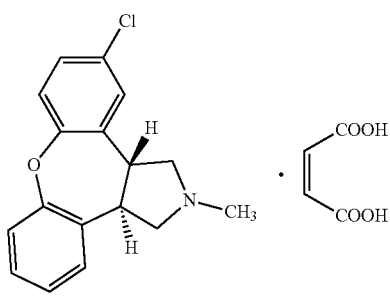

comprising the steps of:
i) cyclization of the intermediate of Formula II

Formula II

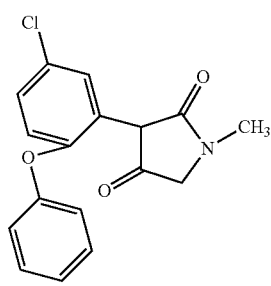

to obtain the intermediate of Formula III

Formula III

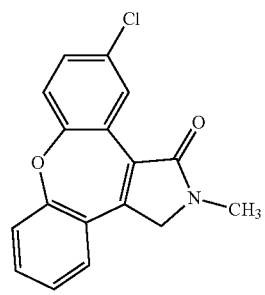

using aluminium halide;

ii) reduction of the double bond of the intermediate of Formula III to obtain the intermediate of Formula IV;

Formula IV

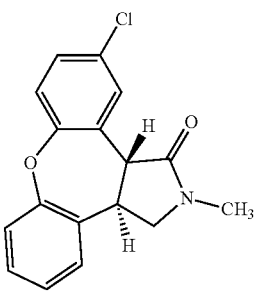

iii) reduction of the keto group of the intermediate of Formula IV to obtain asenapine of Formula V; and Formula V

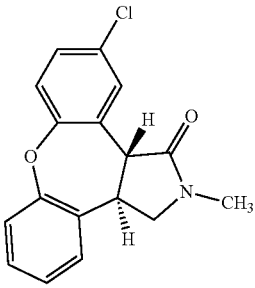

iv) conversion of asenapine of Formula V to asenapine maleate of Formula I.

A third aspect of the present invention provides a process for the preparation of asenapine maleate of Formula I Formula I

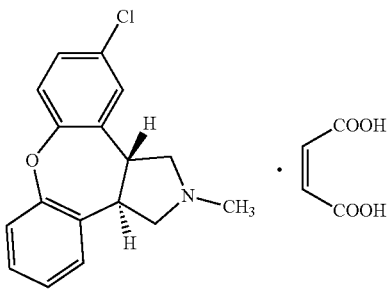

comprising the steps of:
i) cyclization of the intermediate of Formula II

Formula II to obtain the intermediate of Formula III

Formula III

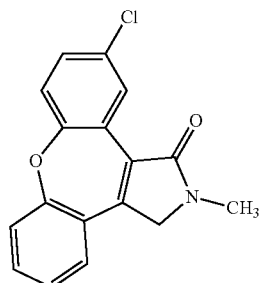

using aluminium halide;
ii) reduction of the double bond of the intermediate of Formula III to obtain the intermediate of Formula IV Formula IV

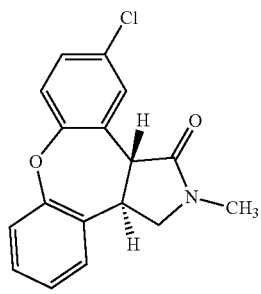

iii) reduction of the keto group of the intermediate of Formula IV using borane dimethyl sulphide to obtain asenapine of Formula V; and Formula V

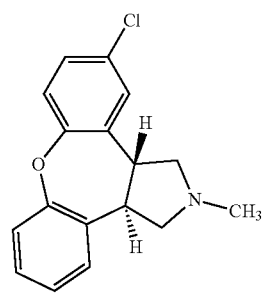

iv) conversion of asenapine of Formula V to asenapine maleate of Formula I.

A fourth aspect of the present invention provides a process for the preparation of asenapine maleate of Formula I Formula I

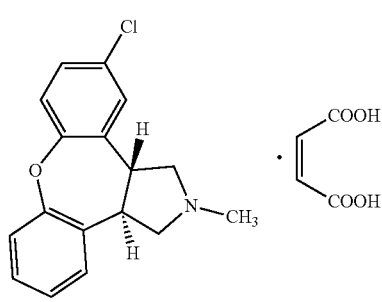

comprising the steps of:
i) cyclization of the intermediate of Formula II

Formula II

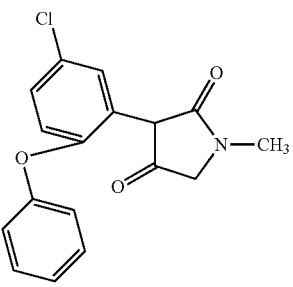

to obtain the intermediate of Formula III

Formula III

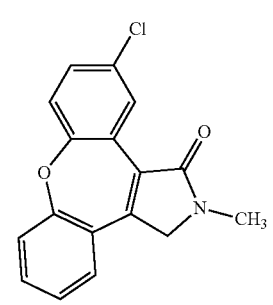

using aluminium halide;
ii) simultaneous reduction of the keto group and the double bond present in the pyrrole moiety of the intermediate of Formula III to obtain asenapine of Formula V; and Formula V

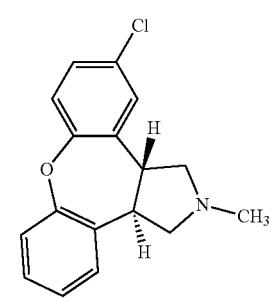

iii) conversion of asenapine of Formula V to asenapine maleate of Formula I.

Other objects, features, advantages and aspects of the present invention will become apparent to those of ordinary skill in the art from the below provided detailed description.

DETAILED DESCRIPTION OF THE INVENTION

The term "ambient temperature", as used herein, refers to a temperature in the range of about 20° C. to 35° C.

The starting intermediate of Formula II may be prepared by the process disclosed in U.S. Pat. No. 4,145,434, which is incorporated herein by reference. In general, the intermediate of Formula II may be prepared by the reaction of ethyl N-[(5-chloro-2-phenoxyphenyl)acetyl]-N-methylglycinate with a metal hydride or a metal alkoxide. Examples of metal hydrides include sodium hydride, lithium aluminium hydride or sodium borohydride. Examples of metal alkoxides include sodium butoxide or potassium butoxide.

Cyclization of the intermediate of Formula II to the intermediate of Formula III may be carried out using anhydrous aluminium halide such as aluminium chloride or aluminium bromide in suitable solvent(s) selected from aromatic hydrocarbons, chlorinated hydrocarbons, ethers or mixtures thereof. Examples of aromatic hydrocarbons include benzene, nitrobenzene, toluene, xylenes, monochlorobenzene or 1,2-dichlorobenzene. Examples of chlorinated hydrocarbons include dichloromethane, chloroform, 1,1,2,2-tetrachloroethane or 1,2-dichloroethane. Examples of ethers include diethyl ether, ethyl methyl ether, di-isopropyl ether or 1,4-dioxane.

Cyclization may be carried out by stirring the reaction mixture containing the intermediate of Formula II and aluminium halide in a suitable solvent at a temperature of about 30° C. to about 110° C., preferably at about 80° C. to about 100° C., for about 1 hour to about 12 hours. The reaction mixture may be cooled to ambient temperature and quenched by dropwise addition of a mixture of water and concentrated hydrochloric acid. The contents may be further stirred for about 15 minutes to about 1 hour. A hydrocarbon solvent, such as hexane or heptane, may be added. The contents may be stirred for about 10 minutes to about 2 hours, filtered and dried. Drying may be accomplished by any suitable method such as air drying, drying under reduced pressure, vacuum tray drying or a combination thereof at ambient temperature to about 80° C. In the preferred embodiments of the present invention, the intermediate of Formula III is air dried at ambient temperature for about 12 hours to 18 hours. The air-dried material may be further dried at about 35° C. to about 65° C. for about 3 hours to about 5 hours under reduced pressure.

Reduction of the double bond of the intermediate of Formula III may be carried out by catalytic hydrogenation, by treatment with magnesium metal turnings in an alcohol, or by Birch reduction.

In a particular embodiment of the present invention, reduction of the double bond may be carried out by treating the intermediate of Formula III with magnesium metal turnings in methanol. The reaction mixture may be refluxed for about 1 hour to about 5 hours, cooled to ambient temperature, slurried in water and filtered. Concentrated hydrochloric acid may be added to adjust the pH followed by extraction with an alkyl acetate or ether solvent to obtain a diastereomeric mixture. Examples of alkyl acetate include ethyl acetate or di-isopropyl acetate. Examples of ether include diethyl ether, ethyl methyl ether or di-isopropyl ether.

Separation of the diastereomeric mixture into cis- and trans-isomers may be carried out using silica gel column chromatography using ethyl acetate-hexane as the eluant.

Reduction of the keto group of the intermediate of Formula IV may be carried out using complex metal hydrides like di-isobutylaluminium hydride, lithium borohydride or sodium trimethoxyborohydride or borane dimethyl sulphide in an organic solvent selected from ether or hydrocarbon. Examples of ether include diethyl ether, ethyl methyl ether, di-isopropyl ether or 1,4-dioxane. Examples of hydrocarbons include benzene, toluene or xylenes.

In a preferred embodiment of the present invention, the reduction of the keto group may be carried out by adding a solution of borane dimethyl sulphide in tetrahydrofuran to a pre-heated solution of the intermediate of Formula IV (heated to about 50° C. to about 80° C.) in tetrahydrofuran at a temperature of about 50° C. to about 80° C. in an inert atmosphere. The reaction mixture may be stirred for about 8 hours to about 16 hours. Dimethyl sulphide produced during the reaction may be slowly distilled-off. Fresh tetrahydrofuran may be added to compensate for the loss of tetrahydrofuran during distillation. An additional amount of borane dimethyl sulphide solution may be added again and the reaction mixture may be stirred for about 1 hour to about 6 hours. An alcohol selected from the group comprising of methanol, ethanol or propanol may be added. The contents may be stirred for about 5 minutes to about 30 minutes followed by addition of a mixture of sulphuric acid and water. The reaction mixture may be stirred at about 60° C. to about 90° C. for about 4 hours to about 10 hours, cooled, extracted with a solvent selected from hydrocarbon solvents such as benzene, nitrobenzene, toluene, xylenes, monochlorobenzene or 1,2-dichlorobenzene and air dried. Water may be added, followed by the slow addition of ammonia solution in about 5 minutes to about 30 minutes. Asenapine of Formula V may be extracted from the reaction mixture by adding a hydrocarbon solvent such as benzene, nitrobenzene, toluene, xylenes, monochlorobenzene or 1,2-dichlorobenzene.

The simultaneous reduction of the keto group and the double bond present in the pyrrole moiety of the intermediate of Formula III to obtain asenapine of Formula V may be carried out using an alkali metal in an alcohol or a mixture of lithium aluminium hydride and aluminium halide.

Conversion of asenapine of the intermediate of Formula V into asenapine maleate of Formula I may be carried out by conventional methods such as the method described in U.S. Pat. No. 4,145,434.

In the foregoing section, embodiments are described by way of examples to illustrate the process of invention. However, these are not intended in any way to limit the scope of the present invention. Several variants of the examples would be evident to persons ordinarily skilled in the art which are within the scope of the present invention.

EXAMPLES

Example 1

Preparation of 11-Chloro-2-methyl-2,3-dihydro-1H-dibenzo[2,3:6,7]oxepino[4,5-C]pyrrol-1-one [Formula III] using Aluminium Bromide and 1,2-dichlorobenzene Anhydrous aluminium bromide (2.5 g) was added to a reaction mixture containing 3-(5-chloro-2-phenoxyphenyl)-1-methylpyrrolidine-2,4-dione (1 g) in 1,2-dichlorobenzene (4 mL) at ambient temperature. The reaction mixture was stirred at about 85° C. for about 9 hours, then cooled to ambient temperature. A mixture of water and concentrated hydrochloric acid (50 mL:5 mL) was added slowly. The contents were stirred for about 30 minutes. Hexane (10 mL) was added. The contents were stirred for about 1 hour, filtered, washed with hexane (10 mL) and dried in air at about 30° C. for about 15 hours to obtain 11-chloro-2-methyl-2,3-dihydro-1H-dibenzo [2,3:6,7]oxepino[4,5-c]pyrrol-1-one.
Yield: 86%

Example 2

Preparation of 11-Chloro-2-methyl-2,3-dihydro-1H-dibenzo[2,3:6,7]oxepino[4,5-C]pyrrol-1-one [Formula III] using Aluminium Chloride and 1,2-dichlorobenzene Anhydrous aluminium chloride (5 g) was added to a reaction mixture containing 3-(5-chloro-2-phenoxyphenyl)-1- methylpyrrolidine-2,4-dione (1 g) in 1,2-dichlorobenzene (5 mL) at ambient temperature. The reaction mixture was stirred at about 85° C. for about 2 hours and 30 minutes, then cooled to ambient temperature. A mixture of water and concentrated hydrochloric acid (50 mL:5 mL) was added dropwise. The contents were stirred for about 30 minutes. Hexane (10 mL) was added. The contents were stirred for about 15 minutes, filtered, washed with hexane (10 mL) and dried in air at about 30° C. for about 15 hours followed by further drying at about 50° C. under reduced pressure to obtain 11-chloro-2-methyl-2,3-dihydro-1H-dibenzo [2,3:6,7]oxepino[4,5-c]pyrrol-1-one.
Yield: 90%

Example 3

Preparation of 11-Chloro-2-methyl-2,3-dihydro-1H-dibenzo[2,3:6,7]oxepino[4,5-C]pyrrol-1-one [Formula III] using Aluminium Chloride and Monochlorobenzene Anhydrous aluminium chloride (5 g) was added to a reaction mixture containing 3-(5-chloro-2-phenoxyphenyl)-1-methylpyrrolidine-2,4-dione (1 g) in monochlorobenzene (1 mL) at ambient temperature. The reaction mixture was stirred at about 98° C. for about 1 hour, then cooled to ambient temperature. A mixture of water and concentrated hydrochloric acid (50 mL:5 mL) was added slowly. The contents were stirred for about 30 minutes. Hexane (50 mL) was added. The contents were stirred for about 1 hour, filtered, washed with hexane (15 mL) and dried in air at about 30° C. for about 15 hours to obtain 11-chloro-2-methyl-2,3-dihydro-1H-dibenzo [2,3:6,7] oxepino [4,5-c]pyrrol-1-one.
Yield: 97%

Example 4

Preparation of Trans-(3a,12b)-11-chloro-2-methyl-2,3,3a,12b-tetrahydro-1H-dibenzo[2,3:6,7]oxepino[4,5-C]pyrrol-1-one [Formula IV]

Magnesium metal turnings (10 g) were added to a suspension of 11-chloro-2-methyl-2,3-dihydro-1H-dibenzo[2,3:6,7]oxepino[4,5-c]pyrrol-1-one (7 g) in methanol (50 mL). The reaction mixture was slowly heated to refluxing temperature. Brisk effervescence was observed. The reaction mixture was cooled to control the reaction and again refluxed for about 2 hours. The reaction mass was diluted with methanol (30 mL), further refluxed for about 30 minutes, cooled to ambient temperature, slurried in water (150 mL) and filtered. pH of the filtrate was adjusted to 1-2 by adding concentrated hydrochloric acid. A clear solution was obtained. The solution was extracted with ethyl acetate (3×50mL) followed by washing with water (3×50 mL). Ethyl acetate was recovered to obtain a mixture of diastereomers as brown oil (4.6 g) followed by separation of the two isomers using silica gel column chromatography eluting with ethyl acetate-hexane mixture.
cis-isomer: 50%
trans-isomer: 9%

Example 5

Preparation of Asenapine [Formula V]

A 2M solution of borane dimethyl sulphide in tetrahydrofuran (128 mL) was added dropwise to a pre-heated solution (heated to about 64° C.) of trans-(3a,12b)-11-chloro-2-methyl-2,3,3a,12b-tetrahydro-1H-dibenzo[2,3:6,7]oxepino[4,5-c]pyrrol-1-one (30 g) in tetrahydrofuran (300 mL) at about 64° C. under nitrogen flow. The reaction was allowed to proceed for about 12 hours. Dimethyl sulphide produced during the reaction was slowly distilled out from the reaction mixture and fresh tetrahydrofuran was added to compensate for the loss of tetrahydrofuran during distillation. Borane dimethyl sulphide in tetrahydrofuran 2M solution (24 mL) was added and the reaction mixture was stirred for about 3 hours for completion of the reaction. Tetrahydrofuran was distilled-off under reduced pressure. Methanol (250 mL) was added to the residue and the reaction mixture was stirred for 15 minutes. Sulphuric acid:water mixture (75 mL:500 mL) was added over a period of about 5 minutes. The reaction mixture was stirred at about 80° C. for about 7 hours, cooled to about 50° C. and washed with toluene (2×200mL). The layers were separated. The aqueous layer was cooled to about 0° C. to 5° C., filtered, washed with ice-cold water (100 mL) and dried in air at about 45° C. for about 15 hours.

29 g of the air-dried material was suspended in water (150 mL) Ammonia solution was added slowly over a period of about 10 minutes. Asenapine was extracted from the reaction mixture by adding toluene (2×100 mL), washing with water (100 mL) followed by distilling-off toluene under reduced pressure.
Yield: 22.2 g

The invention claimed is:

1. A process for the preparation of asenapine maleate of Formula I

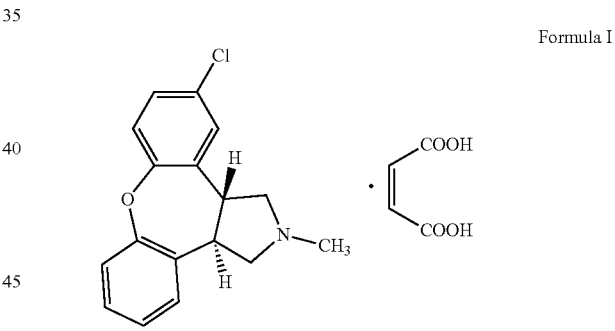

Formula I comprising:
cyclization of the intermediate of Formula II

Formula II to obtain the intermediate of Formula III

Formula III

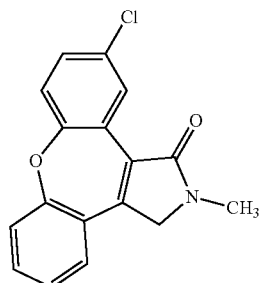

using aluminium halide.

2. A process for the preparation of asenapine maleate of Formula I

Formula I

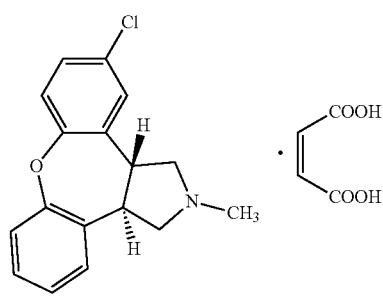

comprising the steps of:
i) cyclization of the intermediate of Formula II

Formula II

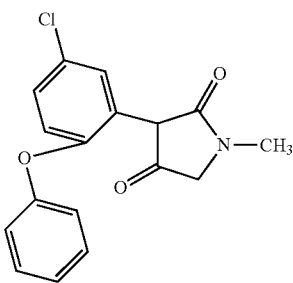

to obtain the intermediate of Formula III

Formula III

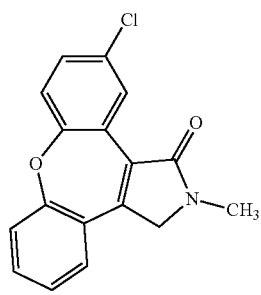

using aluminium halide;

ii) reduction of the double bond of the intermediate of Formula III to obtain the intermediate of Formula IV Formula IV

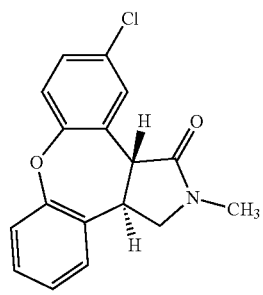

iii) reduction of the keto group of the intermediate of Formula IV to obtain asenapine of Formula V; and Formula V

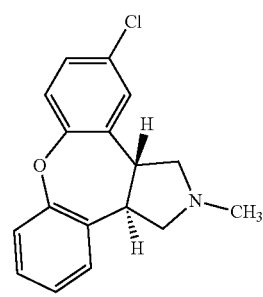

iv) conversion of asenapine of Formula V to asenapine maleate of Formula I.

3. The process according to claim 1 or 2, wherein the aluminium halide is aluminium chloride or aluminium bromide.

4. The process according to claim 1 or 2, wherein the cyclization is carried out in a solvent selected from aromatic hydrocarbons, chlorinated hydrocarbons, ethers, or mixtures thereof.

5. The process according to claim 1 or 2, wherein the cyclization is carried out by stirring at a temperature of about 30° C. to about 110° C.

6. The process according to claim 1 or 2, wherein the cyclization is carried out by stirring for about 1 hour to about 12 hours.

7. The process according to claim 2, wherein reduction of the double bond of the intermediate of Formula III is carried out by catalytic hydrogenation, by treatment with magnesium metal turnings in an alcohol, or by Birch reduction.

8. The process according to claim 2, wherein reduction of the keto group of the intermediate of Formula IV is carried out using complex metal hydrides or borane dimethyl sulphide.

9. The process according to claim 2, wherein reduction of the keto group of the intermediate of Formula IV is carried out in ether or hydrocarbon solvent.

10. The process according to claim 2, wherein reduction of the keto group of the intermediate of Formula IV is carried out at about 50° C. to about 80° C.

* * * * *